United States Patent [19]

Murata et al.

[11] Patent Number: 5,380,908
[45] Date of Patent: Jan. 10, 1995

[54] CONTINUOUS PRODUCTION OF AROMATIC CARBONATES

[75] Inventors: Kiyokazu Murata; Kozo Kawahashi; Mamoru Watabiki, all of Hyogo, Japan

[73] Assignee: Daicel Chemical Industries, Ltd., Osaka, Japan

[21] Appl. No.: 131,679

[22] Filed: Oct. 5, 1993

[30] Foreign Application Priority Data

Oct. 8, 1992 [JP] Japan .................. 4-270238
Nov. 26, 1992 [JP] Japan .................. 4-315477

[51] Int. Cl.[6] .............................. C07C 69/96
[52] U.S. Cl. ............................ 558/270; 558/274
[58] Field of Search .......................... 558/270, 274

[56] References Cited

U.S. PATENT DOCUMENTS 4,045,464  8/1977  Romano et al. ........... 558/274
5,210,268  5/1993  Fukuoka et al. ........... 558/270

*Primary Examiner*—Mary C. Lee
*Assistant Examiner*—Michael G. Ambrose
*Attorney, Agent, or Firm*—Sughrue, Mion, Zinn, Macpeak & Seas

[57] ABSTRACT

A process for continuously producing aromatic carbonates comprising continuously feeding a dialkyl carbonate, an aromatic hydroxy compound, and a catalyst to a reactor equipped with a distillation tower, continuously distilling off a by-produced aliphatic alcohol from the distillation tower so as to keep the aliphatic alcohol concentration in the reactor at 2% by weight or less, and continuously withdrawing produced alkylaryl carbonate and/or diaryl carbonate and the catalyst from the reactor; and a process for continuously producing a diaryl carbonate comprising continuously feeding an alkylaryl carbonate and a catalyst to a reactor equipped with a distillation tower, continuously distilling off a by-produced dialkyl carbonate from the distillation tower so as to keep the dialkylcarbonate concentration in the reactor at 2% by weight or less, and continuously withdrawing the produced diaryl carbonate and the catalyst from the reactor are disclosed. Continuous production of aromatic carbonates can be performed in a stable manner without being accompanied by clogging of a distillation tower.

7 Claims, 2 Drawing Sheets

CONTINUOUS PRODUCTION OF AROMATIC CARBONATES

FIELD OF THE INVENTION

This invention relates to continuous production of aromatic carbonates. More particularly, it relates to a process for continuously producing an alkylaryl carbonate and/or a diaryl carbonate by reacting a dialkyl carbonate and an aromatic hydroxy compound and a process for continuously producing a diaryl carbonate from an alkylaryl carbonate.

BACKGROUND OF THE INVENTION

It is well known that an alkylaryl carbonate undergoes disproportionation to give a diaryl carbonate and a dialkyl carbonate as shown by reaction formula (I):

wherein R represents an alkyl group; and Ar represents an aryl group (hereinafter the same).

It is also well known that an interesterification reaction between an alkylaryl carbonate and an aromatic hydroxy compound yields a diaryl carbonate as shown by reaction formula (II):

Accordingly, an alkylaryl carbonate is indispensable for production of a diaryl carbonate.

An alkylaryl carbonate can be obtained by reacting a dialkyl carbonate and an aromatic hydroxy compound in the presence of a catalyst as depicted by reaction formula (III):

The reactions represented by formulae (I) to (III) are equilibriumreactions with the equilibriumbeing shifted to the original system. Conventional studies on these reactions have been directed chiefly to development of catalysts (see JP-A-51-75044 (which corresponds to U.S. Pat. No. 4,045,464) (the term "JP-A" as used herein means an "unexamined published Japanese patent application"), JP-A-51-105032 (which corresponds to U.S. Pat. No. 4,182,726), JP-A-54-48733, JP-A-60-169444, JP-A-60-169445 (which corresponds to U.S. Pat. No. 4,552,704), JP-A-56-25138, JP-A-57-176932, JP-A-57-183745, JP-A-60-173016 (which corresponds to U.S. Pat. No. 4,609,501), JP-A-1-93560, JP-A-1-265064, and JP-A-1-265064).

Further, in order to help the reaction proceed, it has been proposed to install a distillation tower on the reactor to drive a by-produced alcohol or a carbonate out of the reaction system while conducting the reaction in a batch system (see JP-B-61-25696 (the term "JP-B" as used herein means an "examined published Japanese patent application"), JP-A-60-173016, JP-A-60-169445, JP-A-60-169444, JP-A-56-123948 (which corresponds to U.S. Pat. No. 4,182,726), JP-A-56-25138, JP-A-54-48733, JP-A-54-48732, JP-A-51-105032, and JP-A-51-75044).

It has also been proposed to produce an alkylaryl carbonate and/or a diaryl carbonate by feeding a dialkyl carbonate, an aromatic hydroxy compound, and a catalyst to a multi-plate distillation tower being continuously operated as described in JP-A-3-291257 (which corresponds to U.S. Pat. No. 5,210,268).

However, since the above process attains only a low conversion, large quantities of unreacted dialkyl carbonate and aromatic hydroxy compound separated from the produced aromatic carbonates should be returned to the reaction system. That is, the process requires not only large-sized equipment but increased cost for separation of unreacted materials from the produced aromatic carbonates and is therefore unsuited to industrial production of aromatic carbonates.

It is also well known that an alkylaryl carbonate easily undergoes decarboxylation to produce an alkylaryl ether as is mentioned in JP-A-51-75044. Therefore, heating for a long time causes an untoward side reaction, resulting in a reduction in yield of a diaryl carbonate.

In order to overcome this problem, it has been suggested to carry out the disproportionation reaction of an alkylaryl carbonate (formula (I)) by feeding an alkylaryl carbonate and a catalyst to a multi-plate distillation tower being continuously operated as described in JP-A-4-9358 (which corresponds to U.S. Pat. No. 5,210,268).

However, where a mixture of a dialkyl carbonate, an aromatic hydroxy compound and a catalyst or a mixture of an alkylaryl carbonate and a catalyst is fed to a multi-plate distillation tower in continuous operation as described above, the catalyst precipitates to clog the distillation tower during long-term operation. If a distillation tower in continuous operation is clogged, the tower must be dismantled and cleaned. Dismantling and cleaning of a distillation tower are economically disadvantageous as involving much time and labor. Besides, periodical shut-down of the production line for dismantling and cleaning of a distillation tower involves non-routine work such as resumption and shut-down of equipment, which is unfavorable from the safety consideration.

SUMMARY OF THE INVENTION

An object of the present invention is to provide an improved process for continuously producing an alkylaryl carbonate and/or a diaryl carbonate (hereinafter inclusively referred to as aromatic carbonates) comprising reacting a dialkyl carbonate and an aromatic hydroxy compound in the presence of a catalyst, in which a high reaction rate and a high selectivity can be attained without causing clogging of a distillation tower and thereby achieving continuous production in a stable manner.

Another object of the present invention is to provide an improved process for continuously producing a diaryl carbonate from an alkylaryl carbonate in the presence of a catalyst, in which a high yield and a high selectivity can be attained without causing clogging of a distillation tower and thereby achieving continuous production in a stable manner.

It has now been found that aromatic carbonates can be obtained at a high reaction rate and a high selectivity by continuously feeding a dialkyl carbonate, an aromatic hydroxy compound, and a catalyst to a reactor equipped with a distillation tower, continuously driving out a by-produced aliphatic alcohol from the top of the distillation tower so as to control the aliphatic alcohol concentration in the reactor to 2% by weight or less, and continuously withdrawing produced aromatic carbonates and the catalyst from the reactor. Since the catalyst is fed to the reactor, no clogging of the distillation tower was observed.

With reference to the continuous production of a diaryl carbonate from an alkylaryl carbonate, the present inventors have studied a counter-measure against clogging of a distillation tower, influences of the concentration of a by-produced dialkyl carbonate in a reactor, and a means for suppressing a decarboxylation reaction. As a result, they have found that a diaryl carbonate can be continuously produced from an alkylaryl carbonate in the presence of a catalyst in a high yield at a high selectivity by continuously feeding an alkylaryl carbonate and a catalyst to a reactor equipped with a distillation tower, continuously driving out a by-produced dialkyl carbonate from the distillation tower so as to control the concentration of the dialkyl carbonate in the reactor to 2% by weight or less, and continuously withdrawing a produced diaryl carbonate and the catalyst from the reactor.

DETAILED DESCRIPTION OF THE INVENTION

Figure 1:
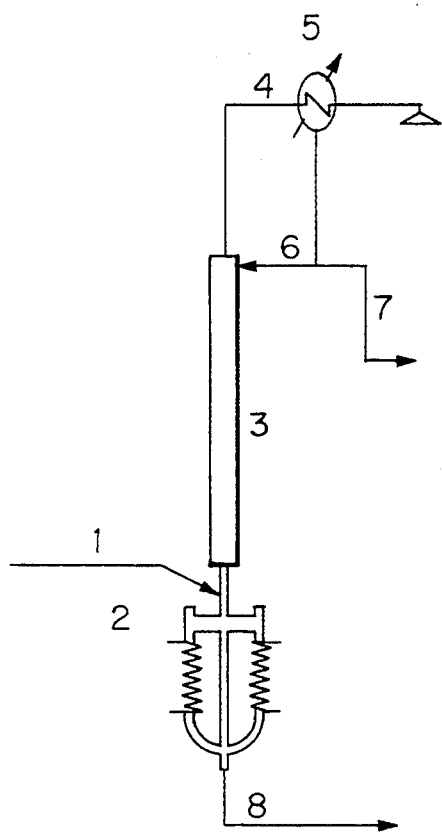
FIG. 1 shows laboratory equipment used in Examples 1 and 2 and Comparative Example 1.

The process for producing aromatic carbonates according to the present invention will be described below in detail.

The aliphatic alcohol concentration in the reactor is controlled to 2% by weight, preferably from 0.001 to 1% by weight, more preferably from 0.01 to 0.1% by weight.

The reaction temperature depends on the operating conditions. Reaction at too low a temperature fails to attain a high reaction rate. Temperatures of not less than 120° C. are recommended. Too high a temperature not only involves difficulty in securing a heating source but causes side reactions. A particularly preferred reaction temperature ranges from 150° to 350° C.

The reaction pressure is preferably from atmospheric pressure up to 100 kg/cm$^2$G, and more preferably from 1 to 20 kg/cm$^2$G.

The retention time in the reactor (a quantity of a residual liquid in the reactor (l) divided by a quantity of a withdrawn liquid per unit time (l/hour)) is usually at least 0.1 hour and preferably from 0.5 to 16 hours. Too long a retention time requires a large-sized reactor.

A recommended molar ratio of a dialkyl carbonate to an aromatic hydroxy compound is from 5/1 to 1/5. It the molar ratio is too high or too low, the unreacted materials to be returned to the reaction system will increase.

A solvent is not necessarily needed. If necessary, for ease of reaction and operation, an inert solvent, such as an aliphatic hydrocarbon, an aromatic hydrocarbon, an ether, a halogenated aliphatic hydrocarbon or a halogenated aromatic hydrocarbon, may be employed.

For effective driving out of the by-produced aliphatic alcohol, a gas or a low-boiling organic compound which is inert to the reaction may be introduced into the reactor. An azeotropic agent which forms an azeotrope with the aliphatic alcohol may be added to the reaction system.

The process for producing a diaryl carbonate according to the present invention will be described below.

JP-A-4-9358 which teaches a process for conducting the disproportionation reaction by feeding an alkylaryl carbonate and a catalyst to a multi-plate distillation tower in continuous operation has a mention of occurrence of decarboxylation in a long time reaction. Notwithstanding, such a decarboxylation reaction hardly occurred when an alkylaryl carbonate and a catalyst were continuously fed to a reactor equipped with a distillation tower. The reasons therefor seem to be as follows:

1) Since the disproportionation reaction of an alkylaryl carbonate proceeds rapidly in the presence of a catalyst, the concentration of the alkylaryl carbonate which is liable to decarboxylation in the reactor is reduced.

2) By performing the reaction in a continuous system but not in a batch system, the substantial retention time of the alkylaryl carbonate which is liable to decarboxylation in the reactor is reduced.

In order to prove the above assumptions, the inventors determined the disproportionation rate constant of methylphenyl carbonate and estimated the time required for reaching the equilibrium at 195° C. It was found as a result that the reaction comes to equilibrium in 2 to 3 minutes.

Since the by-produced dialkyl carbonate is to be removed as a distillate from the top of the distillation tower, a dialkyl carbonate having a lower boiling point than those of a starting alkylaryl carbonate and a produced diaryl carbonate is used in the present invention.

The dialkyl carbonate recovered as a distillate may be a mixture containing the starting alkylaryl carbonate or the produced diaryl carbonate. In this case, however, the alkylaryl carbonate or diaryl carbonate must be afterward separated from the dialkyl carbonate in a separate process. Accordingly, it is preferable to operate so as not to incorporate the alkylaryl carbonate or the diaryl carbonate into the distillate.

An increase of the concentration of a dialkyl carbonate in the reactor makes the reaction shift to the original system which does not favor production of a diaryl carbonate. As a result of the inventors' investigation, it has been found that a diaryl carbonate can be obtained in a high yield by maintaining the dialkyl carbonate concentration in the reactor at 2% by weight or less by distillation. The dialkyl carbonate concentration in the reactor is preferably controlled in the range of from 0.001 to 1% by weight, more preferably from 0.01 to 0.1% by weight. The residue withdrawn from the reactor may contain an alkylaryl carbonate or an aromatic hydroxy compound in addition to a catalyst.

Figure 3:
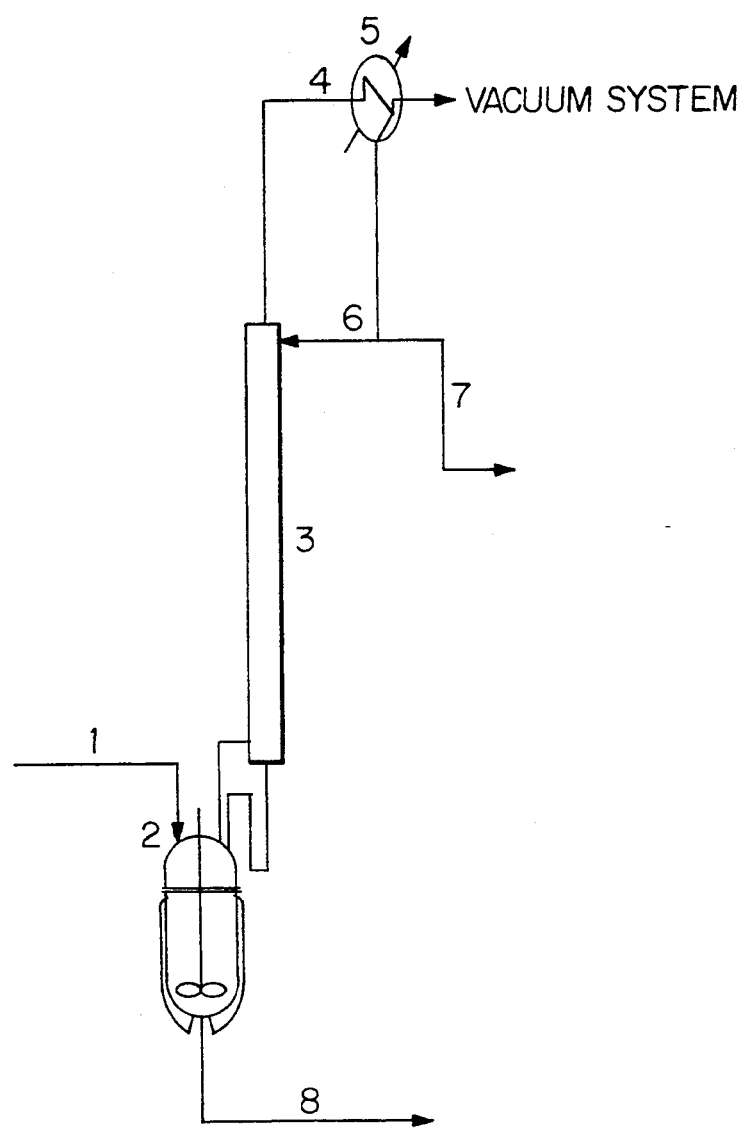
FIG. 3 shows laboratory equipment used in Examples 4 to 6 and Comparative Examples 2 to 3.

The concentration of the dialkyl carbonate in the distillate may be increased by increasing a reflux ratio (refluxing amount/distillated amount) of the distillation tower, but too high a reflux ratio needs much heat to increase the production cost. In FIG. 3, the refluxing amount is an amount returned to the distillation tower 3 through pipe 6 and the distillated amount is an amount driven out of the distillation tower 3 through 7. A recommended reflux ratio is from 0 to 20 and preferably from 0 to 10.

The reaction temperature usually ranges from 50° to 300° C., and preferably from 100° to 250° C., while varying depending on the kind and the composition of the starting material.

The reaction pressure is usually within a range of from 50 mmHg to 100 kg/cm$^2$G, while varying depending on the kind and the composition of the starting material and the reaction temperature.

The retention time in the reactor is usually from 0.1 to 20 hours, and preferably from 0.3 to 10 hours, while depending on the reaction temperature and the kind and the composition of the starting material.

A solvent is not necessarily needed. If necessary, for ease of reaction and operation, an inert solvent, such as an aliphatic hydrocarbon, an aromatic hydrocarbon, an ether, a halogenated aliphatic hydrocarbon or a halogenated aromatic hydrocarbon, may be employed.

For effective driving out of the by-produced dialkyl carbonate, a gas or a low-boiling temperature-having organic compound which is inert to the reaction may be introduced into the reactor.

The starting material (alkylaryl carbonate) may contain an aromatic hydroxy compound. It may also contain the produced diaryl carbonate or dialkyl carbonate, but cares should be taken not to increase too much the concentrations of the diaryl carbonate or dialkyl carbonate in the reaction system because a disproportionation reaction is a reversible reaction and too high concentrations of these products cause a reduction of the conversion of the starting alkylaryl carbonate.

The details of the starting materials, catalysts and production equipment which can be used to carry out the processes of the present invention are described below.

The dialkyl carbonate which can be used in the present invention are represented by formula:

ROCOR wherein R represents an alkyl group, an aliphatic group, an aralkyl group, etc.; the two R's may be the same or different.

The alkyl group, aliphatic group or aralkyl group as represented by R may be substituted with, for example, a lower alkyl group (C$_1$ to C$_5$), a lower alkoxy group (C$_1$ to C$_5$), a cyano group, a halogen atom, etc. and may contain therein an unsaturated bond.

Specific examples of the alkyl group are methyl, ethyl, propyl (inclusive of all the isomers), allyl, butyl (inclusive of all the isomers), butenyl (inclusive of all the isomers), pentyl (inclusive of all the isomers), hexyl (inclusive of all the isomers), heptyl (inclusive of all the isomers), octyl (inclusive of all the isomers), nonyl (inclusive of all the isomers), decyl (inclusive of all the isomers), and cyclohexylmethyl groups. Specific examples of the aliphatic group are cyclopropyl, cyclobutyl, cyclopentyl, cyclohexyl, and cycloheptyl groups. Specific examples of the aralkyl group are benzyl, phenethyl (inclusive of all the isomers), phenylpropyl (inclusive of all the isomers), phenylbutyl (inclusive of all the isomers), and methylbenzyl (inclusive of all the isomers) groups.

Specific but non-limiting examples of the dialkyl carbonate include dimethyl carbonate, diethyl carbonate, dipropyl carbonate (inclusive of all its isomers), dibutyl carbonate (inclusive of all the isomers), diallyl carbonate, dibutenyl carbonate (inclusive of all the isomers), methylethyl carbonate, methylpropyl carbonate (inclusive of all the isomers), methylbutyl carbonate (inclusive of all the isomers), ethylpropyl carbonate (inclusive of all the isomers), ethylbutyl carbonate (inclusive of all the isomers), dibenzyl carbonate, ethylene carbonate, and propylene carbonate.

The alkylaryl carbonate which can be produced by the present invention is represented by formula:

ROCOAr wherein R is as defined above; and Ar represents a monovalent aromatic group, such as a phenyl group, an alkylphenyl group, an alkoxyphenyl group, a halogenated phenyl group, a naphthyl group, a substituted naphthyl group, a heterocyclic aromatic group, and a substituted heterocyclic aromatic group.

Specific examples of the alkylphenyl group as represented by Ar include tolyl, xylyl, trimethylphenyl, tetramethylphenyl, ethylphenyl, propylphenyl, butylphenyl, diethylphenyl, methylethylphenyl, pentylphenyl, hexylphenyl, and cyclohexylphenyl groups, each inclusive of all their several isomers. Specific examples of the alkoxyphenyl group as Ar include methoxyphenyl, ethoxyphenyl and butoxyphenyl groups, each inclusive of all their isomers. Specific examples of the halogenated phenyl group as Ar include fluorophenyl, chlorophenyl, bromophenyl, chloro(methyl)phenyl and dichlorophenyl groups, each inclusive of all their isomers. Specific examples of the substituted or unsubstituted naphthyl groups as Ar include naphthyl, methylnaphthyl, dimethylnaphthyl, chloronaphthyl, methoxynaphthyl and cyanonaphthyl groups, each inclusive of all their isomers. Specific examples of the substituted or unsubstituted heterocyclic aromatic group as Ar include pyridyl, coumaryl, quinolyl, methylcoumaryl and methylquinolyl groups, each inclusive of all their isomers.

Combination of R and Ar in the above formula gives a variety of alkylaryl carbonates.

R is preferably an alkyl group containing from 1 to 4 carbon atoms, and Ar is preferably an aromatic group containing from 6 to 10 carbon atoms. While not limiting, preferred examples of the alkylaryl carbonate include methylphenyl carbonate, ethylphenyl carbonate, propylphenyl carbonate, butylphenyl carbonate, allylphenyl carbonate, methyltolyl carbonate, ethyltolyl carbonate, propyltolyl carbonate, butyltolyl carbonate, methylxylyl carbonate, ethylxylyl carbonate, propylxylyl carbonate, and butylxylyl carbonate, each inclusive of all their isomers if present.

The diaryl carbonate which can be produced according to the present invention is represented by formula:

ArOCOAr wherein Ar is as defined above; the two Ar's may be the same or different.

While not limiting, specific examples of the diaryl carbonate include diphenyl carbonate, ditolyl carbonate, dixylyl carbonate, dinaphthyl carbonate, phenyltolyl carbonate, and di(ethylphenyl) carbonate, each inclusive of all their isomers if present.

The catalyst which can be used in the present invention is not particularly limited as long as it catalyzes a reaction between a dialkyl carbonate and an aromatic hydroxy compound to produce an alkylaryl carbonate and/or a diaryl carbonate and also catalyzes an intramolecular interesterification (disproportionation) and intermolecular interesterification of an alkylaryl carbonate to produce a diaryl carbonate and a dialkyl carbonate.

Catalysts which might have been precipitated to clog a distillation tower in the conventional continuous production of aromatic carbonates due to their low solubility in the liquid existing in the reaction system as well as catalysts which are soluble in the starting materials and the reaction products can be used in the present invention.

The added amount of the catalyst is preferably from 0.006 to 20% by weight based on the reaction mixture in the reactor.

Specific examples of suitable catalysts are shown below for illustrative purposes only but not for limitation.

Organotin Compounds $(CH_3)_3SnOCOCH_3$, $(C_2H_5)_3SnOCOPh$, $Bu_3SnOCOCH_3$, $Ph_3SnOCOCH_3$, $Bu_2Sn(OCOCH_3)_2$, $(C_2H_5)_3SnOH$, $Ph_3SnOH$, $Bu_2SnO$, $(C_8H_{17})_2SnO$, $Bu_2SnCl_2$, and $BuSnO(OH)$.

wherein Ph represents a phenyl group; and Bu represents a butyl group (hereinafter the same)

Lead Compounds $PbO$, $PbO_2$, $Pb_3O_4$, $PbS$, $PbS_2$, $Pb(OH)_2$, $Pb_2O_2(OH)_2$, $Na_2PbO_2$, $NaHPbO_2$, $Na_2PbO_3$, $Na_2H_2PbO_4$, $K_2pbO_3$, $PbCO_3$, $Pb(OH)_2$, $Bu_4Pb$, $Ph_4Pb$, $Ph_3Pb$, $Bu_3PbOH$, $Bu_3PbCl$, $Pb(OCH_3)_2$, $(CH_3O)Pb(OPh)$, $Pb(OPh)_2$, Pb-Na, Pb-Ca, Pb-Sn, and Pb-Sb.

Copper Compounds $CuCl$, $CuCl_2$, $CuBr$, $CuBr_2$, $CuI$, $CuI_2$, $Cu(OAc)_2$, $Bu_2Cu$, and $(CH_3O)_2Cu$.

wherein Ac represents an acetyl group.

Iron Series Metal Compounds $Fe(C_{10}H_8)(CO)_5$, $Fe(CO)_5$, and $Fe(C_4H_6)(CO)_5$.

Lewis Acid Compounds $AlX_3$, $TiX_3$, $TiX_4$, $ZnX_2$, $FeX_5$, $SnX_5$, $SnX_4$, and $VX_5$.

Others

Metal complexes of acetylacetate
wherein X represents a halogen atom, an acetoxy group, an alkoxy group or an aryloxy group.

Any reactor in which a liquid phase reaction can be carried out (inclusive of a reaction in a slurry containing a catalyst) can be used in the present invention. Illustrative examples of applicable reactors include a tank reactor, a tower reactor, a fluidized bed reactor, and a reboiler of a distillation tower.

Any kind of distillation towers as meant in chemical engineering can be used in the present invention. Illustrative examples of usable plate distillation towers include a bubble cap tower, a sieve tower, and a bubble tower. Fillers for packed distillation towers include Raschig ring, pole ring, Berl saddle, interlock saddle, Dixon packing, MacMahon packing, Sulzer packing, and Mellapak.

The present invention will now be illustrated in greater detail by way of Examples, but the present invention should not be construed as being limited thereto.

EXAMPLE 1

The laboratory apparatus used in this Example is shown in FIG. 1. The apparatus is composed of 800 ml-volume thermosyphon type reboiler (reactor) 2, glass-made Oldshue distillation tower 3 (40 mm $\phi \times 20$ plates), and condenser 5 set at the top of the distillation tower.

A mixture of dimethyl carbonate (hereinafter abbreviated as DMC), phenol (hereinafter abbreviated as PhOH) and dibutyltin oxide ($Bu_2SnO$) as a catalyst were continuously fed to reactor 2 through pipe 1 to conduct a reaction under atmospheric pressure. The reaction mixture containing the produced methylphenyl carbonate (hereinafter abbreviated as MPC) and diphenyl carbonate (hereinafter abbreviated as DPC) was continuously withdrawn from the bottom of reactor 2 through pipe 8 at a controlled rate so as to keep the amount of the liquid in reactor 2 at 700 ml. By-produced methanol was introduced to condenser 5 through pipe 4 and condensed there. Part of the condensate was continuously refluxed to the top of distillation tower 3 through pipe 6 while continuously distilling off the rest of the condensate through pipe 7. The distillate contained DMC, the starting material.

After the operation was continued in this way for consecutive 720 hours, no clogging of the perforated trays of the tower was observed.

The reaction conditions and the results obtained are shown in Table 1 below.

COMPARATIVE EXAMPLE 1

A reaction was conducted in the same manner as in Example 1, except for feeding a mixture of DMC, PhOH and a catalyst to distillation tower 3 at the 7th plate from the top. Although the reaction results were equal to those obtained in Example 1, a part of the perforated trays of the plates lower than the plate where the DMC/PhOH/catalyst mixture was fed was found clogged after 720 hours' operation.

EXAMPLE 2

A reaction was conducted in the same manner as in Example 1, except for changing the reaction conditions as shown in Table 1. The reaction results are shown in the Table.

EXAMPLE 3

Figure 2:
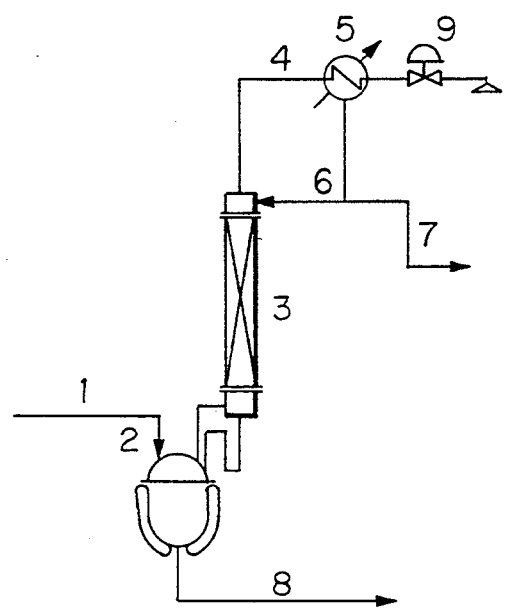
FIG. 2 shows laboratory equipment used in Example 3.

The laboratory apparatus used in this Example is shown in FIG. 2. The apparatus is composed of 1200 ml-volume stainless steel-made tank reactor 2 which also serves as a reboiler, stainless steel-made distillation tower 3 (inner diameter:28 mm; packing height:2380 mm) packed with Dixon packing (6 mm), and condenser 5. Numeral 9 in FIG. 2 is an automatic pressure-control valve.

The operating pressure was set at 6 atm, and a mixture of DMC, PhOH, and dibutyltin oxide as a catalyst was continuously fed to reactor 2 through pipe 1 to conduct a reaction. The reaction mixture containing MPC and DPC was continuously withdrawn from the bottom of reactor 2 through pipe 8 at a controlled rate so as to keep the amount of the liquid in reactor 2 at 620 ml. By-produced methanol was introduced to condenser 5 through pipe 4 and condensed there. Part of the condensate was continuously refluxed to the top of distillation tower 3 through pipe 6 while continuously distilling off the rest of the condensate through pipe 7. The distillate contained the starting DMC.

The reaction conditions and the reaction results are shown in Table 1.

By-produced DMC was continuously introduced to condenser 5 through pipe 4 and condensed there. Part of the condensate was refluxed to the top of distillation tower 3 through pipe 6, and the rest of the condensate was continuously withdrawn through pipe 7. The distillate contained anisole as a by-product of decarboxylation. The selectivity to anisole was found to be 1% based on the reacted MPC.

After the operation was continued under the above

TABLE 1

| Example No. | Reaction Conditions | | | Starting Material | | |
|---|---|---|---|---|---|---|
| | Tower Top Pressure (atm) | Tower Bottom Temp. (°C.) | Reflux Ratio | DMC Feed Rate (g/h) | PhOH Feed Rate (g/h) | Catalyst (Amount) (mmol/kg) |
| 1 | 1 | 128 | 40 | 216.8 | 226.5 | $Bu_2SnO$ (32) |
| 2 | 1 | 137 | 40 | 108.4 | 113.3 | $Bu_2SnO$ (32) |
| 3 | 6 | 204 | 40 | 244.4 | 255.0 | $Bu_2SnO$ (24) |

| Example No. | Distillate | | Residue | | | | PhOH Conversion (%) |
|---|---|---|---|---|---|---|---|
| | Flow Rate (g/h) | Alcohol (Content) (wt %) | Flow Rate (g/h) | Composition | | | |
| | | | | MPC (wt %) | DPC (wt %) | MeOH (wt %) | |
| 1 | 28 | MeOH (9.8) | 415.3 | 3.3 | — | 0.03 | 3.8 |
| 2 | 24.7 | MeOH (14.2) | 194.0 | 7.6 | 0.6 | 0.03 | 9.0 |
| 3 | 30.7 | MeOH (73.9) | 468.7 | 19.7 | 2.8 | 0.14 | 26.9 |

As proved by the results in Table 1, the present invention makes it possible to achieve the reaction between a dialkyl carbonate and an aromatic hydroxy compound in the presence of a catalyst for the production of aromatic carbonates at a high conversion in a high yield without being accompanied by clogging of a distillation tower.

EXAMPLE 4

The laboratory apparatus used in this Example is shown in FIG. 3. The apparatus is composed of 800 ml-volume reactor 2 equipped with a stirrer, Oldshue distillation tower 3 (40 mm $\phi \times 40$ plates), and condenser 5 set at the top of the distillation tower.

A mixture of MPC and dibutyltin oxide as a catalyst was continuously fed to reactor 2 through pipe 1 to conduct a reaction. The reaction mixture containing DPC was continuously withdrawn from the bottom of reactor 2 through pipe 8 at a controlled rate so as to keep the amount of the liquid in reactor 2 at 620 ml.

conditions for consecutive 720 hours, no clogging of the perforations of the Oldshue distillation tower was observed. The conversion of MPC was 76%. The reaction conditions and the results obtained are shown in Table 2 below.

EXAMPLE 5

Ethylphenyl carbonate (hereinafter abbreviated as EPC) was reacted in the same manner as in Example 4 except for the alterations of the reaction conditions shown in Table 2. The conversion of MPC was 80%. The reaction results are also shown in the Table.

EXAMPLE 6

A reaction was conducted in the same manner as in Example 4, except that the volume of the reactor was changed to 5 l and the amount of the liquid in the reactor was maintained at 5 l. The MPC conversion was 84%. The reaction conditions and the results are shown in Table 2.

TABLE 2

| Example No. | Reaction Conditions | | | Starting Material | | Catalyst (Amount) (mmol/kg) |
|---|---|---|---|---|---|---|
| | Tower Top Pressure (mmHg) | Tower Bottom Temp. (°C.) | Reflux Ratio | Feed Rate (g/h) | ROC-(=O)OAr[1] (Concn.) (wt %) | |
| 4 | 200 | 194 | 20 | 214 | MPC (99) | $Bu_2SnO$ (12.8) |
| 5 | 200 | 198 | 20 | 237 | EPC (99) | $Bu_2SnO$ (12.8) |
| 5 | 200 | 195 | 2 | 2100 | MPC (99) | $Bu_2SnO$ (12.8) |

| Example No. | Distillation Rate (g/hr) | Residue | | | Selectivity[4] to ArOC-(=O)OA (%) |
|---|---|---|---|---|---|
| | | Flow Rate (g/hr) | Composition | | |
| | | | ArOC-(=O)OAr[2] (wt %) | ROC-(=O)OR[3] (wt %) | |
| 4 | 45 | 168 | DPC | DMC | 99 |

TABLE 2-continued

| | | | | | |
|---|---|---|---|---|---|
| 5 | 65 | 171 | (66) DPC | (1.8) DEC[5] | 99 |
| | | | (70) | (1.1) | |
| 5 | 510 | 1609 | DPC | DMC | 99 |
| | | | (76) | (1.0) | |

Note:
[1] Alkylaryl carbonate
[2] Diaryl carbonate
[3] Dialkyl carbonate
[4] The ratio of the alkylaryl carbonate which was converted to the diaryl carbonate to the total alkylaryl carbonate having being reacted.
[5] Diethyl carbonate

COMPARATIVE EXAMPLE 2

A reaction was conducted in the same manner as in Example 4, except for feeding a mixture of MPC and a catalyst to distillation tower 3 at the 7th plate from the top. The reaction results were equal to those in Example 4. After 720 hours' continuous operation, a part of the perforated trays of the plates lower than the plate where the MPC/catalyst mixture was fed were found clogged.

COMPARATIVE EXAMPLE 3

A reaction was conducted in the same manner as Example 4, except for keeping the DMC concentration in the reaction mixture at about 3%. Although the selectivity to DPC was 99%, making no difference from that in Example 4, the conversion of MPC was as low as 58%.

Thus, the present invention makes it possible to produce a diaryl carbonate from an alkylaryl carbonate in the presence of a catalyst in a good yield without being accompanied by clogging of a distillation tower.

While the invention has been described in detail and with reference to specific examples thereof, it will be apparent to one skilled in the art that various changes and modifications can be made therein without departing from the spirit and scope thereof.

What is claimed is:

1. A process for continuously producing an alkylaryl carbonate and/or a diaryl carbonate comprising continuously feeding a dialkyl carbonate, an aromatic hydroxy compound, and a catalyst to a reactor equipped with a distillation tower, wherein the production is carried out continuously distilling off a by-produced aliphatic alcohol from the distillation tower so as to keep the aliphatic alcohol concentration in the reactor at 2% by weight or less, and continuously withdrawing produced alkylaryl carbonate and/or diaryl carbonate and the catalyst from the reactor.

2. A process as claimed in claim 1, wherein the molar ratio of said dialkyl carbonate to said aromatic hydroxy compound is from 5/1 to 1/5.

3. A process as claimed in claim 1, wherein the production is carried out at a temperature of from 150° C. to 350° C.

4. A process for continuously producing a diaryl carbonate comprising continuously feeding an alkylaryl carbonate and a catalyst to a reactor equipped with a distillation tower, wherein the production is carried out continuously distilling off a by-produced dialkyl carbonate from the distillation tower so as to keep the dialkylcarbonate concentration in the reactor at 2% by weight or less, and continuously withdrawing the produced diaryl carbonate and the catalyst from the reactor.

5. A process as claimed in claim 4, wherein the production is carried out at a temperature of from 50° to 300° C.

6. A process as claimed in claim 4, wherein the reflux ratio of the production is from 0 to 20.

7. A process as claimed in claim 4, wherein the retention time of the production from 0.1 to 20 hours.

* * * * *